(12) United States Patent
Cuschieri et al.

(10) Patent No.: US 7,025,389 B2
(45) Date of Patent: Apr. 11, 2006

(54) METHOD AND DEVICE FOR TRANSFERRING FLUID

(75) Inventors: Ian J. Cuschieri, Hurstbourne Tarrant (GB); Jean-Marc Sibenaler, Anderlecht (BE); Joost M. Vancaillie, Lombise (BE); Thierry Baltus, Verlaine (BE)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 18 days.

(21) Appl. No.: 10/457,332

(22) Filed: Jun. 6, 2003

(65) Prior Publication Data

US 2004/0260266 A1    Dec. 23, 2004

(51) Int. Cl.
*F16L 33/00*    (2006.01)
(52) U.S. Cl. .................... 285/243; 285/3; 285/322
(58) Field of Classification Search ............ 285/3; 604/905
See application file for complete search history.

(56) References Cited

U.S. PATENT DOCUMENTS

| | | | | |
|---|---|---|---|---|
| 4,610,469 A | * | 9/1986 | Wolff-Mooij | 285/3 |
| 4,792,163 A | * | 12/1988 | Kulle | 604/905 |
| 4,895,570 A | | 1/1990 | Larkin | |
| 4,973,328 A | * | 11/1990 | Smith | 604/905 |
| 5,122,123 A | * | 6/1992 | Vaillancourt | 604/905 |
| 5,423,775 A | * | 6/1995 | Cannon | 604/905 |
| 5,437,650 A | * | 8/1995 | Larkin et al. | 604/905 |
| 5,507,733 A | | 4/1996 | Larkin et al. | |
| 5,513,882 A | | 5/1996 | Lewis | |
| 5,562,616 A | | 10/1996 | Haber et al. | |
| 5,566,729 A | | 10/1996 | Grabenkort et al. | |
| 5,775,671 A | | 7/1998 | Cote, Sr. | |
| 5,839,715 A | * | 11/1998 | Leinsing | 604/905 |
| 6,036,171 A | | 3/2000 | Weinheimer et al. | |
| 6,063,068 A | * | 5/2000 | Fowles et al. | 604/905 |
| 6,068,617 A | | 5/2000 | Richmond | |
| 6,142,446 A | | 11/2000 | Leinsing | |
| 6,210,359 B1 | | 4/2001 | Patel et al. | |
| 6,261,282 B1 | | 7/2001 | Jepson et al. | |
| 6,409,708 B1 | | 6/2002 | Wessman | |
| 6,602,239 B1 | | 8/2003 | Ronneklev | |

\* cited by examiner

*Primary Examiner*—David Bochna
(74) *Attorney, Agent, or Firm*—Jeffrey C. Nichols; Joseph P. Reagen; Austin J. Foley

(57) ABSTRACT

A method and device for facilitating fluid communication between a sealed container having an access port and at least one fluid passageway. The device includes a connector provided with a body that defines a fluid passageway between first and second ends of the body. The first end of the body is configured for receiving the fluid source, and the second end is configured for receiving an access port of the container. A locking member is associated with the body and prevents movement of the body relative to the access port when the locking member is in a locked position. The device can be used for the transfer of cytotoxic or other drugs (i.e., fluids) to the container and may remain attached to the access port and used to administer a drug from the container to a patient by means of an administration set with a male luer connector.

20 Claims, 5 Drawing Sheets

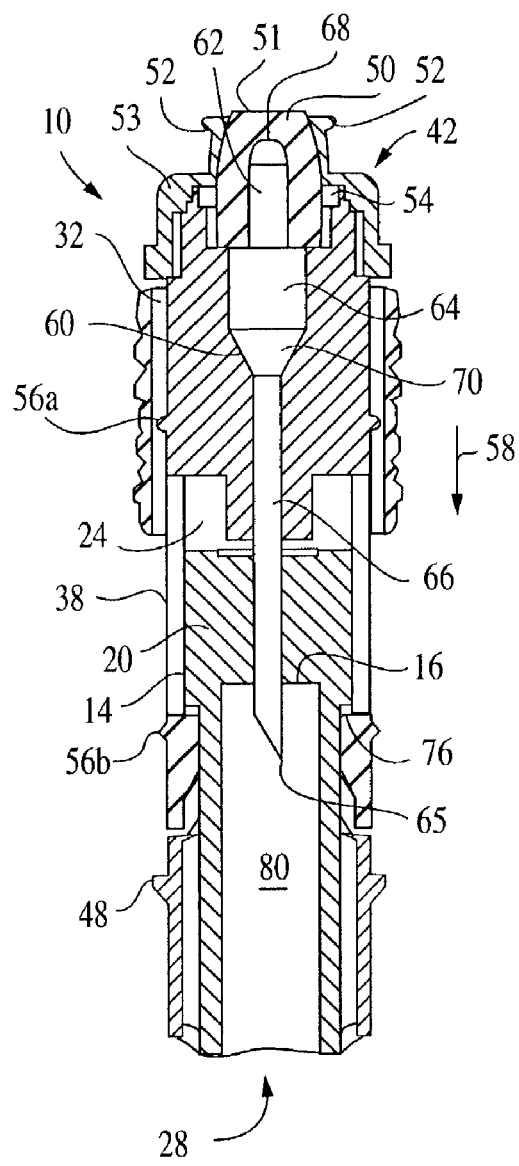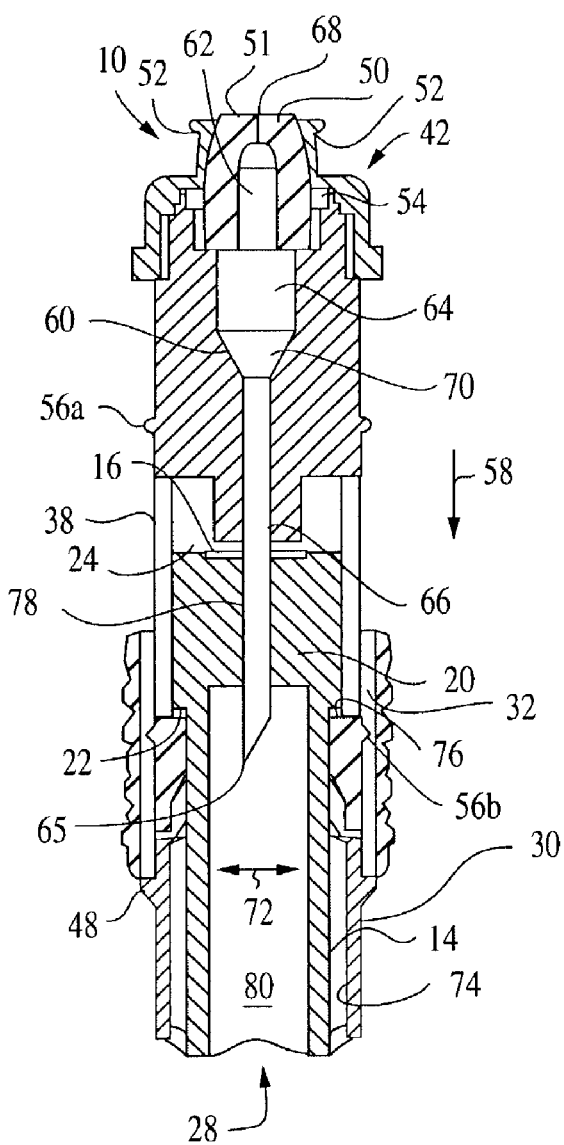
FIG. 2
FIG. 3

METHOD AND DEVICE FOR TRANSFERRING FLUID

FIELD OF THE INVENTION

The present invention relates generally to a method and device for establishing needle-free access to a medication port on an infusion solution container, and more specifically to a method and device for providing a locked, multiple accessible, needle-free connection to the medication port of an infusion solution container and subsequently needle or spike-free delivery of a fluid or solution to a patient.

BACKGROUND OF THE INVENTION

A common method of health care therapy is infusion or intravenous ("I.V.") therapy, whereby fluids possessing desired medication or other characteristics are infused into a patient over varying lengths of time. I.V. therapy generally requires a source container of a fluid, an administration set and a catheter. This method of infusion therapy requires that a connection be made between these components for the transfer of fluid, along a fluid passageway, from a fluid source to a patient.

In addition, infusion therapy frequently requires one of the solutions, which is to be administered to be formulated in the source container according to a certain prescription intended to provide benefit to the patient. Frequently this prescription is compounded by injecting medicaments into a container, which is partially filled with a diluent. Most of these containers presently include a medication port and an administration port. The medication port includes a solid rubber septum, which is penetrated by a needle attached to the end of a syringe, which contains the medicament, and the medicament is then injected through the septum into the diluent. Frequently multiple medicaments are injected into such a container.

Many medicaments pose a hazard to health care workers. Cytotoxic drugs used for chemotherapy pose a significant effect to workers due to their highly toxic properties. Moreover, using needles to puncture the septum in the medicament port poses a needle-stick hazard, which is only compounded by the presence of highly toxic fluids.

One widely used connector for establishing a connection between the administration set and a catheter and to provide a fluid passageway is a luer connection assembly in which mating male and female components are releasably joined. In addition, syringes are generally manufactured with a male luer connector onto which the female luer needle is attached. The luer connector has a blunt tip, which does not pose a health hazard.

Recently, devices for establishing a luer connection to a vial containing lypholized drugs have been used. These connectors eliminate the need for the health care worker to penetrate the stopper of the drug vial with a needle in constituting and withdrawing the medicament. However, if the resulting liquid medicament must be injected into a medication port, the worker must then affix a needle to the syringe luer tip thus presenting the needle hazard.

However, use of a medication port having a solid rubber septum provides many desirable benefits. Use of the solid septum has been shown to prevent the microbial ingress even when the container is subjected to terminal sterilization of the container by high pressure steam or handling during distribution and use. In addition, the smooth outer surface allows the health care worker to easily wipe the septum prior to connection, thus promoting sterility.

However, a solid rubber septum cannot be penetrated by a luer tip. In addition, there are other needle-free connection systems such as a blunt cannula and slit septum system which does not pose a needle-stick hazard but such a blunt cannula cannot penetrate a solid rubber septum. In addition, there is also a risk of drug spillage when the administration port is accessed by a spike of an administration set being used to administer a drug to the patient.

Thus, it is an object of the present invention to provide a method and device for allowing needle-free access to the medicament port of a container and to use this device for the administration of a solution. A more particular object is to provide such a method and device which allows multiple needle-free accesses to the medicament port of a container.

Another object of the present invention is to provide a method and device which allows access to the medicament port of the container without exposing the health care worker to a needle-stick hazard. A more particular object of the present invention is to provide a method and device to allow a luer tip or blunt cannula to access the medicament port of the present container.

A still further object of the present invention is to provide a device meeting the above discussed objects while still preserving the benefits supplied by a solid elastomeric septum, including the benefit that the sterile passageway through the lumen and the luer fittings prior to use is sealed against microbial ingress during use.

BRIEF SUMMARY OF THE INVENTION

A method and device is disclosed for facilitating fluid communication between a sealed container having an access port, such as an I.V. container, and at least one fluid passageway. Transferred fluid can be any number of intravenous fluids possessing desired medication or other characteristics that are infused into a patient, generally over time.

The device includes a connector having a body that has one end configured for receiving the fluid source and another end for engaging the access port of the container. Between the ends of the body is a fluid passageway or lumen that facilitates fluid flow therethrough. The body further includes a locking member that prevents movement of the body relative to the access port of the container. Preventing movement between the locking member and the access port insures that while the connector is securely attached to the access port, multiple connections and disconnections can be performed with a male luer (e.g., a syringe) to provide a closed or locked connection for fluid transfer without a risk of needle puncture or contamination. The connector is also designed to be accessed by an I.V. administration set with a luer lock to allow spike or needle free access to the container, and a secure locked connection and delivery of the solution to the patient.

BRIEF DESCRIPTION OF THE DRAWINGS

FIG. 2 is a vertical sectional view of the connector of FIG. 1 in an unlocked position and shown connected to a tubular member of the I.V. container;

FIG. 3 is a section view of the connector of FIG. 2 shown in a locked position and connected to the tubular member;

DETAILED DESCRIPTION OF THE INVENTION

The present connector provides a fluid passageway to a container for improved reconstitution and administration of fluids, including toxic drugs. One feature of the device which includes a connector is that it can be connected to a tubular member of the container that includes an access port, such as an I.V. container, and prevent movement of a body of the connector relative to the tubular member. Such connection offers an advantage in that while the connector is attached to the access port, multiple insertions can be performed with a medical insertion device or fitting, for example a syringe. In preferred embodiments, the locking member can be axially, or alternatively radially repositioned with respect to the fluid passageway of the body to fix the body relative to the access port, and provide a sealed connection. To further illustrate the preferred broader aspects of the invention, a preferred embodiment of the invention that includes additional inventive features will now be discussed with reference to the drawings.

Figure 1:
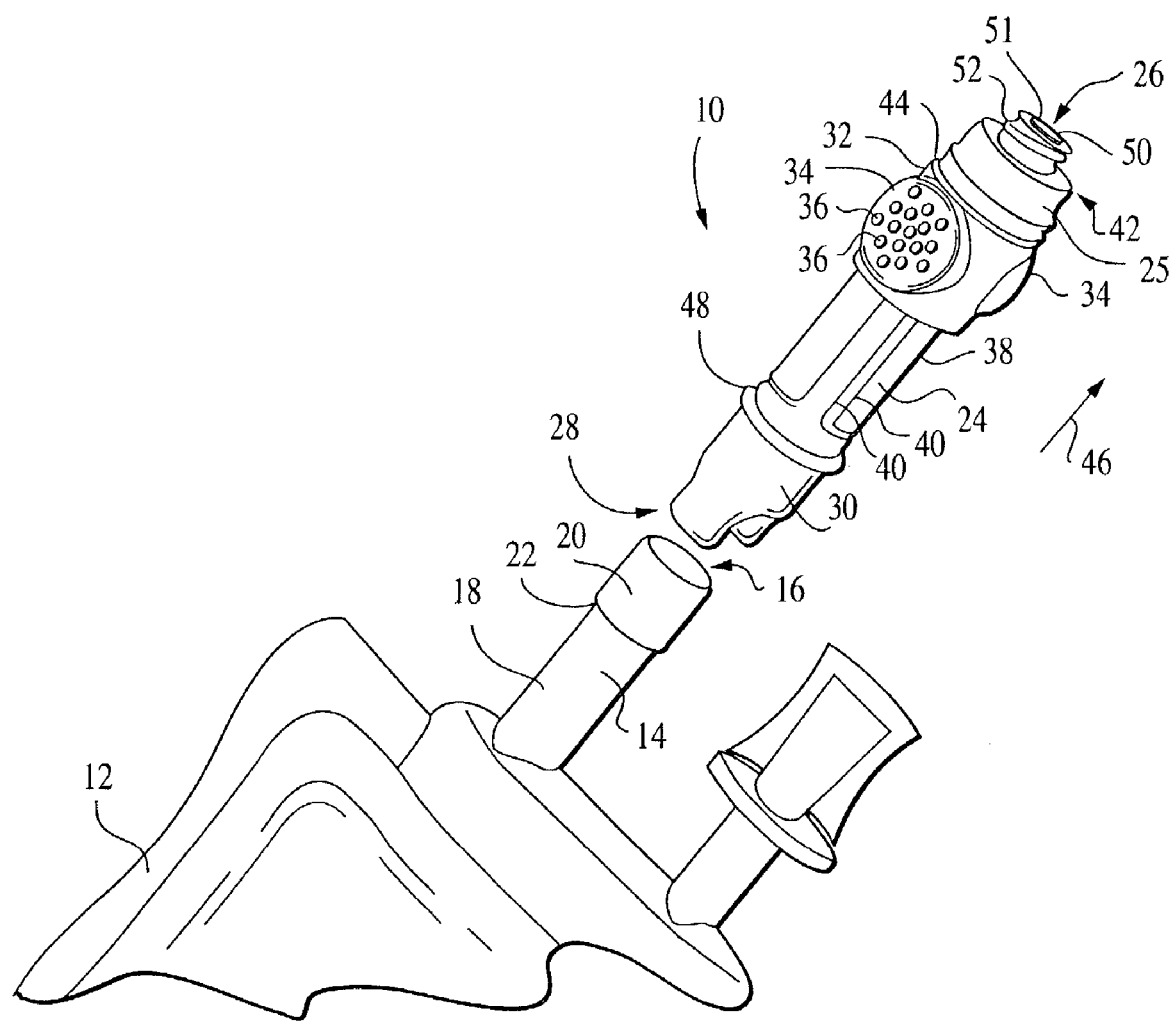
FIG. 1 is a fragmentary exploded perspective view of an I.V. container and a connector according to an embodiment of the present invention.

Turning now to FIG. 1, a preferred embodiment of the present connector is generally designated 10, and is intended for use in establishing a positive sealed connection with an administration set or a container, such as an I.V. container 12. A generally tubular member 14 of the I.V. container 12 forms an access port, generally designated 16. The access port 16 is configured for allowing a fluid to flow therethrough and into the I.V. container 12. Preferably, the tubular member 14 includes a first cylindrical portion 18 and a second cylindrical portion 20, wherein the second cylindrical portion has a greater diameter relative to the first cylindrical portion to define a shoulder 22 therebetween. The connector 10 transfers a fluid, such as cytotoxic or other drugs, from a fluid source (not shown) to the access port 16 of the I.V. container 12 via a body 24 of the connector.

The body 24 is formed in a generally cylindrical shape and includes a fluid receiving portion 25 at a first end 26 that is configured for receiving the fluid source. Opposite the first end 26, the body has a second end 28 configured for engaging the access port 16 of the I.V. container 12. While shown as cylindrical, the body 24 may be provided in other shapes, including having polygonal sides and/or being curved or angled between the ends 26, 28. Preferably, the second end 28 is dimensioned to provide a friction fit between a lower portion 30 of the connector 10 and the second cylindrical portion 20 of the I.V. container 12.

A locking member 32 is associated with the body 24 and prevents movement of the body, and in particular movement of the lower portion 30 relative to the access port 16 or the shoulder 22 of the I.V. container 12 upon a complete or full insertion of the tubular member 14 into the body 24. In the preferred embodiment, the locking member 32 is configured for sliding relative to the body 24 between unlocked and locked positions. In the preferred embodiment, the locking member 32 is cylindrically shaped and is formed to have a diameter greater than that of the body to facilitate the sliding engagement. However, the shape of the locking member 32 is not critical as long as sliding action relative to the body 24 is obtained. Preferably, the locking member 32 includes a pair of gripping surfaces 34 that are inwardly or concavely-shaped towards the body 24 for assisting the user in sliding the locking member. In the preferred embodiment, the gripping surfaces include optional dimples 36 for facilitating gripping action by a user, such as a health care worker.

The body 24 further includes an outer surface 38 that is formed with a plurality of axial ridges 40 that are preferably used to align the locking member 32 during the sliding movement along the outer surface. A female luer and cap assembly 42 is connected to the body 24 and forms a radially projecting rim 44 that limits upward sliding axial movement of the locking member 32 in a direction of an arrow 46. Similarly, a stop, for example an annular ridge 48 or the like, limits downward movement of the locking member 32 in a reverse direction to the arrow 46. The body 24 also includes a septum 50, which is attached to the body by the female luer and cap assembly 42. As is known in the art, the septum 50 enables a male luer or fluid injecting device, for example a syringe (not shown), to be inserted into the body 24 to inject fluid therein. Another example is a male luer tip of an administration set (FIG. 7) for connecting the I.V. container 12 to a patient.

Referring now to FIG. 2, preferably an end 51 of the septum 50 is formed as a generally flat surface to allow for the end to be readily wiped by a health care worker to promote sterility. The septum also includes threads 52 that may connect to a male luer lock of an administration set (not shown) and prevent inadvertent disconnection of the administration set. Moreover, the male luer lock connection of the administration set can be attached to the end 51 after a formulation has been made so that exposure of the formulation to a health care worker is minimized.

In FIG. 2, the connector 10 is shown in an unlocked position, in which the locking member 32 is adjacent a luer cap 53. The luer cap 53 encloses a female luer 54 of the assembly 42, and substantially encloses the septum 50. At least one tactile indicator or radially projecting formation, such as projecting formations 56a, 56b, is provided on the outer surface 38 of the body 24 to facilitate the positing of the locking member 32. In the preferred embodiment, the formations 56a, 56b are contemplated as being individual, spaced projections or teats, or a unitary ring-like projection. That is, the projecting formations 56a, 56b may be included to releasably fix the locking member 32 in a locked or unlocked position, and provide an indication to a user of the locked or unlocked status. In addition to indicating locking status, the annular projecting formations 56a, 56b engage the locking member 32 to prevent undesired sliding movement, such as in an axial direction of an arrow 58, or the reverse direction depending on the position of the locking member.

The connector 10 also includes an internal fluid passageway, generally designated 60 between the ends 26, 28 of the body 24. The fluid passageway 60 includes a first radial inner chamber 62 adjacent the septum 50 that feeds fluid into to a second radial inner chamber 64. In turn, the second chamber 64 may feed the fluid to a piercing member, such as a needle 66, which is at least partially enclosed by the body 24 of the container 10. To prevent potential needlestick injury it is preferred that a pointed end 65 of the needle 66 is contained well within the body 24. The fluid passageway 60 is formed such that the needle 66 pierces the access port 16, which then enables fluid flow through the access port 16 and into the I.V. container 12 or another end source. In addition, a threaded annular locking collar 116, such as the threaded annular locking collar 116 partially shown in FIG. 2 and fully illustrated in FIG. 7, can be connected to the threads 52 to enable connection of an administration set to the connector 10.

One feature of the present connector 10 is that multiple accesses to the septum 50 to inject multiple fluids are possible. That is, the connector 10 may be used during reconstitution of a drug vial with a pre-assembled luer connection (e.g., Biodome injection), for complete needleless reconstitution and for single dose and multi dose additions. Moreover, the I.V. container 12 with the attached connector 10 may be used as a pooled concentrate to multi dose from the I.V. container to one or more additional I.V. containers.

In operation, a male luer (e.g., a syringe), blunt cannula or other preferably needle-free medication delivery device is inserted through an opening or a slit 68 of the septum 50 which is depressed to transfer fluid from the male luer to the internal chambers 62, 64. The fluid is then funneled from the internal chamber 64 by a funnel-shaped portion 70 of the internal chamber 64 to the needle 66, which transfers the fluid in the direction of the arrow 58 to the tubular member 14 and the I.V. container 12.

Referring now to FIG. 3, the connector 10 is shown in a locked position, with the locking member 32 displaced in the direction of the arrow 58 and seated at the lower end 28 of the body 24. In the locked position, the locking member 32 engages the radially projecting formation 56b. In addition, the locking member 32 is stopped from further movement in the direction of the arrow 48 by the annular ridge 48. In operation, the locking member 32 slidingly engages the body 24 and can be moved between the unlocked position illustrated in FIG. 2 and the locked position illustrated in FIG. 3. The reciprocal sliding movement of the locking member 32 is preferably axially aligned with the body 24. Once locked, the lower portion 30 of the connector 10 is prevented by the locking member 32 from moving radially outwards in the direction of arrows 72. This ensures that an inner surface 74 of the body 24, which forms a shoulder 76, engages the shoulder 22 of the tubular member 14 and prevents movement of the body relative to the access port 16 and the tubular member 14. That is, when the locking member 32 is near the access port end 28 of the body 24, the tubular member 14 is sealingly fixed to the connector 10 to facilitate fluid flow into a container, such as the I.V. container 12.

The slit 68 of the septum 50 may extend axially or be orientated at an angle relative to the arrow 58. In addition, the slit 68 may be curved slightly or helically rotated to promote the sealing of the opening when a male luer is not inserted therethrough. As can be appreciated, when a male luer extends through the slit 68 and within the connector 10, the size of the connector and its components are constrained within the spacing between the slit 68 and the funnel-shaped portion 70 of the internal chamber 64.

To minimize any fluid flow restriction, a passageway or lumen 78 through the needle 66 may feed into the inner chamber 64 and an inner passageway 80 of the tubular member 14 without any valves or other obstructions to fluid flow. Preferably, the septum 50 deforms and stretches to facilitate insertion of a male luer through the slit 68. However, the septum 50 must be configured in size to seal before, during, and after extension of the fluid injecting device through the slit 68 to form a closed fluid path. In one embodiment, the septum 50 can be formed of an elastic, resilient material that facilitates insertion of a male luer therethrough, with or without lubrication. Also, in an alternate embodiment the septum 50 may be formed to facilitate insertion of a blunt cannula.

Figure 4:
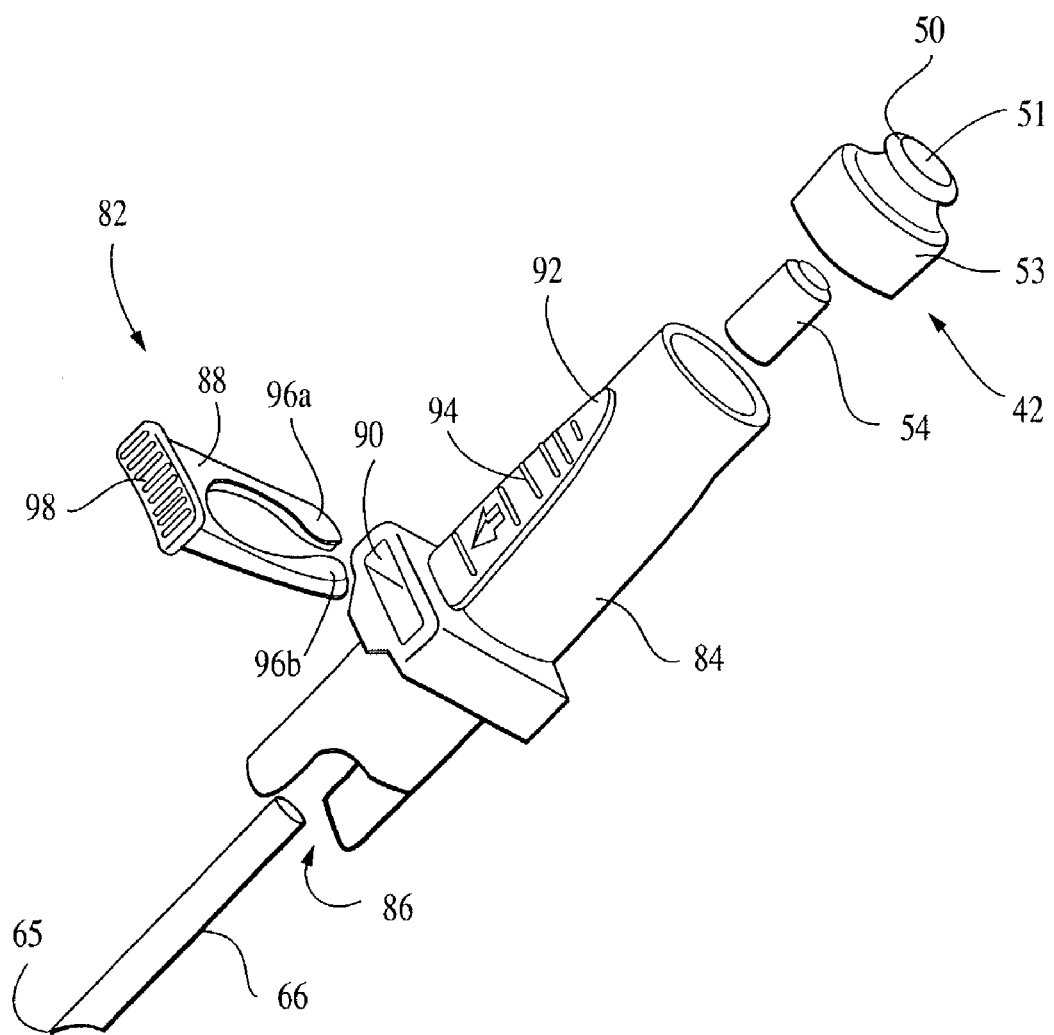
FIG. 4 is an exploded perspective view of an alternative embodiment of the present connector.

Referring now to FIG. 4, an alternative embodiment of the present connector is generally designated 82. Components common to the connecter 10 of FIG. 1 and the connector 82 are provided with identical reference numerals. The connector 82 has a septum 50 and a luer cap and female luer assembly 42. The assembly 42 includes the luer cap 53 and the female luer 54, which connect to a body 84 of the connector 82. An opening 86 in the body 82 engages an access port (not shown) of a container, such as the access port 16 of the I.V. container 12 of FIG. 1. Also included is the needle 66 with the pointed end 65 which is positioned within the body 84 such that the pointed end 65 is enclosed to prevent potential needle-stick injury.

An important distinction between the connectors 10 and 82 is that, in the latter, a locking member 88 is laterally, rather than axially, engaged in an aperture 90 defined by the body. Furthermore, the formation of the septum 50 in the present embodiment can include an end 51 that is configured to accept several different types of luer activating connection designs including, but not limited to, a male luer tip and/or a blunt cannula. Preferably, the body 84 also has gripping members 92 provided with at least one protrusion 94 for facilitating user gripping of the connector 82.

The locking member 88 is preferably dimensioned to be slidingly insertable into the aperture 90 of the body 84. In one embodiment, the locking member 88 can be formed as a C-shaped clip having arms 96a, 96b that are configured for engaging a tubular member, for example the tubular member 14 of FIG. 1, upon insertion of the locking member into the aperture 90 to a closed position (Best seen in FIG. 6). The locking member 88, also preferably includes an optional gripping surface 98 that facilitates insertion and removal of the locking member from the body 84.

Figure 5:
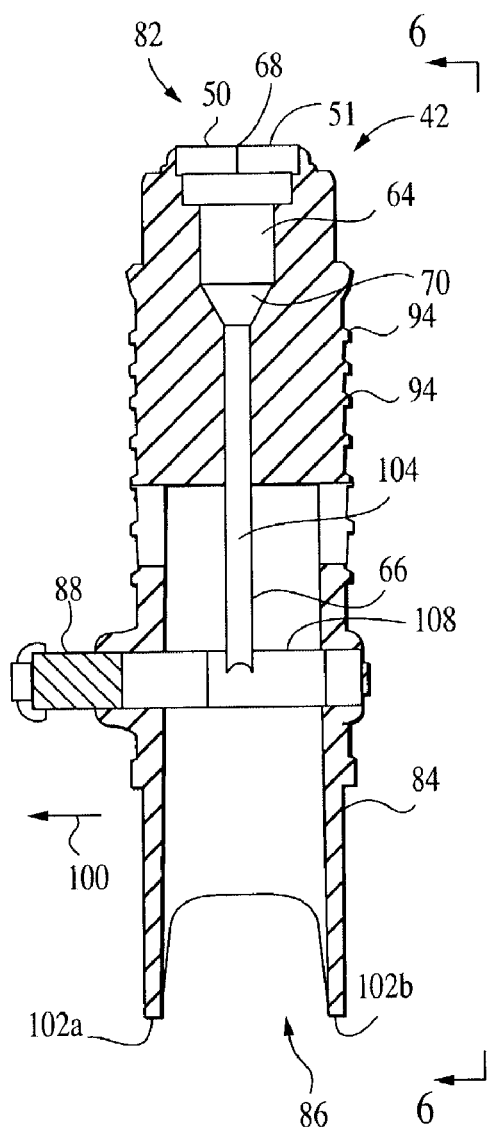
FIG. 5 is a vertical cross-section of the connector of FIG. 4.
Figure 6:
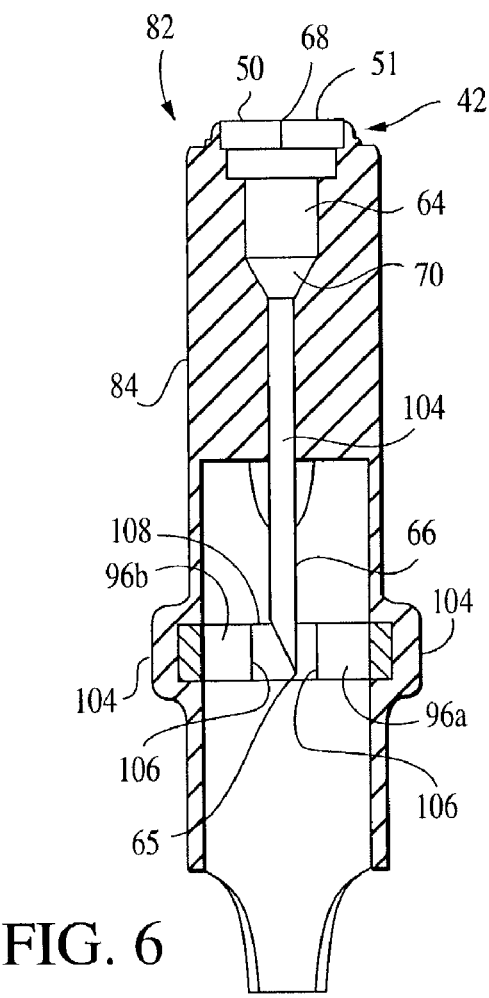
FIG. 6 is a cross-section view taken along lines 6—6 of FIG. 5 and in the direction generally indicated.

Referring now to FIGS. 5 and 6, the connector 82 is shown in an unlocked position with the locking member 88 moved in a radial direction of an arrow 100. In this position, the end arms 96a, 96b of the locking member 88 disengage from the shoulder 22 of the I.V. container 12 of FIG. 1. The locking member 88 is radially moveable relative to the body 84 between a locked position as illustrated from a different perspective in FIG. 6, and the unlocked position illustrated in FIG. 5. Moreover, in the unlocked position, the locking member 88 may be moved in a direction of the arrow 100 to completely disengage the locking member from the body 84 and provide easy disconnection of the connector 82 from an I.V. container or the like.

The body 84 has contoured ends 102a, 102b that facilitate engagement upon the I.V. container 12, which passes through the opening 86. Similar to axial passageway 60 of FIG. 2, the body 84 has the needle 66 positioned internally to allow fluid flow through the needle and to the funnel-shaped portion 70 of the internal chamber 64, which is configured to receive fluid transferred from an external fluid source, such as a male luer or deliver fluid from the I.V. container 12 through an administration set (FIG. 7) to an external source. The male luer may be inserted through the slit 68 of the septum 50 and then pass through the luer cap and female luer assembly 42 to inject fluid into the inner chamber 64. Inserted fluid is then directed by the funnel-shaped portion 70 through a lumen 104 of the needle 66. Similar to the connector 10 of FIG. 1, when the connector 82 is attached to a tubular member of a container, the needle 66 pierces an access port of the tubular member to enable fluid passing through the lumen 104 to be deposited into the container. Turning now to FIG. 6, the body 84 of the connector 82 has a generally rectangular portion 104 that prevents outward radial movement of the arms 96a, 96b upon insertion of the locking member 88 into the body 84.

In use, the connector is placed upon the tubular member (e.g., the tubular member 14 of FIG. 1). Next, the locking member 88 is inserted through the aperture 90 of FIG. 4 to engage the tubular member 14. Upon engagement, an inner surface 106 of the arms 96a, 96b abuts against the tubular member 14 to prevent movement (e.g., radial and axial movement) of the tubular member relative to the body 84. Protruded portions 104 of the body 84 further reinforce abutment of the arms 96a, 96b against the tubular member 14 by preventing radial outward movement of the arms. Axial movement is preferably prevented by having an upper surface 108 of the locking member 88 engage a shoulder 22 of the tubular member 14 similar to the arrangement depicted in FIG. 2.

Figure 7:
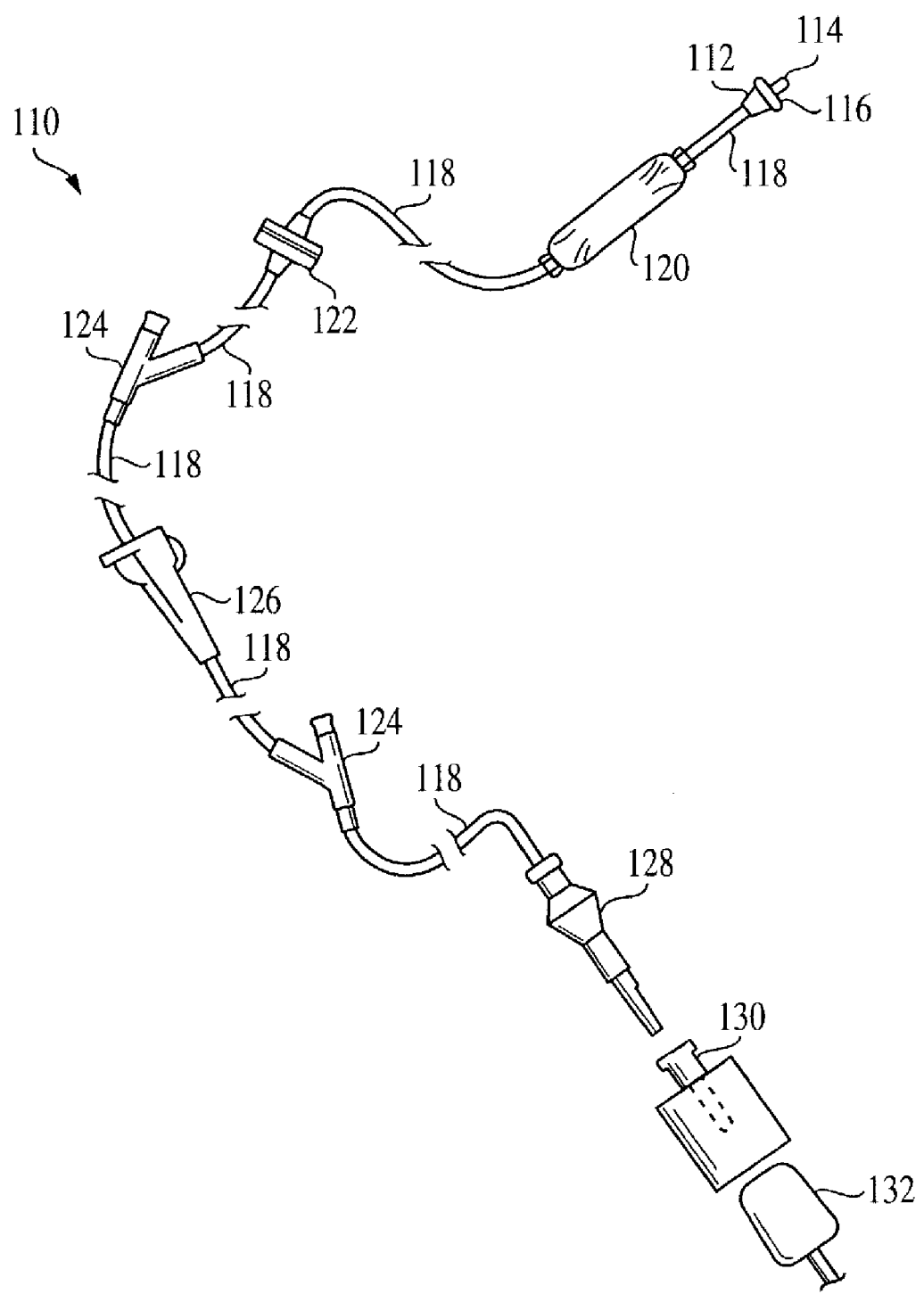
FIG. 7 is a fragmentary exploded view of an administrative set suitable for use with the present connector.

Thus, it will be seen that the present connectors 10, 82 and locking members 32, 88 provide improved connectors for transferring fluid from a male luer (or as discussed earlier, a blunt cannula) to a container, such as an I.V. container and also the ability to deliver fluid from the I.V. container to an external source via an administration set, generally designated as 110 in FIG. 7. The connectors 10, 82 reduce the risk of needle puncture or contamination when administering cytotoxic fluids to a patient. Moreover, another advantage of the connectors 10, 82 is that while they are attached to an access port multiple leak-free connections and disconnections can be performed with a male luer.

Referring now to FIG. 7, the administration set 110 includes a male luer tip 112 that connects to the connector 10. More particularly, an end portion or access port 114 of the male luer tip 112 passes through the end 51 (FIG. 1) of the connector 10 and is prevented from further insertion into the luer cap 53 by the threaded annular locking collar 116 which surrounds the male luer tip and is configured for threadably engaging the threads 52 of the septum 50. The fastening of the locking collar 116 to the septum 50 prevents fluid leakage by holding the male luer tip 112 in engagement with the septum. Tubing, generally designated as 118, connects various components of the administrative set 110. These components include a drip chamber 120, a check valve 122, at least one Y-site 124, a roller clamp 126, and a blunt cannula 128.

The drip chamber 120 is generally tubular and has an upper end cap (not shown) and a lower end cap (also not shown). The upper end cap includes a formation for establishing a fluid connection with an upstream portion of the administration set 110, and the lower end cap includes a formation for establishing a fluid connection with a downstream portion of the administration set. The upper end cap typically has a drop former (not shown) which is designed to produce droplets of a desired volume of the fluid as the fluid flows through the upper end cap and through the dip chamber 120. Then, by adjusting the fluid flow so that a desired number of droplets pass through the drip chamber 120 in a certain period of time, a desired rate of volume and administration may be accomplished.

The check valve 122 generally permits one-way fluid flow through the administration set 10, and blocks fluid flow in a direction toward the drip chamber 120. The Y-sites 124 can be used to attach a secondary administration set (not shown) to the administration set 110 and combine two fluids. The roller clamp 126 controls fluid flow (i.e., start or stop) through the administration set 110.

The blunt cannula 128 creates a fluid flow path through an injection site 130 which connects to a catheter 132. Commonly, the catheter 132 is inserted into a vein of a patient to allow fluid communication with the administration set 1 10. Thus, the administration set 110 can be considered as a fluid conduit that provides a fluid to the connector 10, and vice-versa. For example, the connector 10 can be accessed by the male luer tip 112 of the administration set 110 to allow spike or needle-free access to a container, such as the I.V. container 12, and provide a secure locked connection and delivery of a fluid to and from a patient.

While particular embodiments of the connector have in shown and described, it will be appreciated by those skilled in the art that changes and modifications may be made there too without departing from the invention and its broader aspects and as set forth in the following claims.

The invention claimed is:

1. A connector for facilitating repeated fluid communication between a sealed container or other fluid flow device having a pierceable access port and at least one fluid passageway for transferring a fluid between a fluid source and the pierceable access port of the container or other device, comprising:
   a body having a first end configured for receiving a fluid, a second end for receiving the pierceable access port of the container, a first projection disposed at a first position between said first and second ends, a second projection disposed at a second position between said first and second ends, a sharpened cannula defining at least a portion of a fluid passageway between said first and second ends and at least partially enclosed by said body to prevent inadvertent user contact therewith, a needle-less access septum carried at said first end and in fluid communication with said sharpened cannula, said needle-less access septum being accessible by a needle-free delivery device; and
   a locking member including opposed ends, wherein said locking member is associated with said body and movable between a first or unlocked position and a second or locked position for preventing movement of said body relative to the pierceable access port, and wherein said locking member releasably engages the first projection between said opposed ends when in the first position and engages the second projection between said opposed ends when in the second position.

2. The connector of claim 1 wherein said locking member slidingly engages said body between said first or unlocked position and said second or locked position.

3. The connector of claim 2 wherein said second position is near said second end to prevent radial movement of a lower portion of said body upon engagement with the pierceable access port.

4. The connector of claim 2 wherein said locking member is axially slidable along said body between said first and second positions.

5. The connector of claim 1 wherein said first end and needle-less access septum are configured to sealingly receive a male luer tip.

6. The connector of claim 1 wherein said first end and needle-less access septum are configured for sealingly receiving a blunt cannula.

7. The connector of claim 1 further comprising a luer cap attached to said body and configured for sealing said first end.

8. The connector of claim 1 wherein said sharpened cannula is a needle having a lumen therethrough.

9. The connector of claim 8 wherein said needle has a pointed end enclosed by said body.

10. A connector for transferring a fluid between a fluid injecting device and a pierceable access port of a container or other fluid flow device comprising:
    an elongated body having a first end with a needle-less access septum configured for receiving a needle-free fluid injecting device that injects fluid into said elongated body and a second end for receiving the pierceable access port of the container;
    means for transferring the fluid injected into said elongated body to the pierceable access port, wherein said transferring means is in fluid communication with the needle-less access septum and a portion of the body at least partially encloses said transferring means to prevent inadvertent user contact therewith; and
    means for preventing movement of said elongated body relative to the pierceable access port to facilitate transfer of the fluid to the pierceable access port, wherein the means for preventing movement of said elongated body comprises a locking member disposed between said first and second ends and movable at an angle with respect to the elongated body between a first or unlocked position contacting the elongated body and a second or locked position, and wherein said locking member is perpendicularly slidable into said body between said first or unlocked position and said second or locked position.

11. A connector for providing fluid communication between an external source and a container or other medical fluid flow device including a generally tubular member having a shoulder separating different radial portions of the tubular member, the connector comprising:
    a body having a first portion for receiving a fluid from the external source and a second portion for receiving the tubular member, said body defining a fluid passageway having a longitudinal axis within said first and second receiving portions;
    a needle-less access septum carried at said first portion of said body and communicating with said fluid passageway;
    an access member associated with said second portion for accessing the tubular member, said second portion at least partially enclosing said access member to prevent inadvertent user contact therewith; and
    a locking member disposed between said first and second portions and moveable at an angle with respect to the longitudinal axis of said fluid passageway between a first or unlocked position contacting the body and a second or locked position for engaging said tubular member to prevent movement of said second portion relative to the shoulder of the tubular member.

12. The connector of claim 11 wherein said needle-less access septum allows fluid flow into the body upon insertion of a blunt cannula into the needle-less access septum and prevents fluid flow into the body when the blunt cannula is removed.

13. The connector of claim 11 wherein said needle-less access septum is configured to sealingly receive a male luer tip.

14. The connector of claim 11 wherein said access member is in communication with said fluid passageway for transferring the fluid passed into said body and to the tubular member.

15. The connector of claim 14 wherein said access member is a needle having a lumen therethrough.

16. The connector of claim 15 wherein said needle has a pointed end enclosed by said body.

17. A device for facilitating fluid communication between a sealed container or other medical fluid flow device having a pierceable access port and at least one fluid passageway, comprising:
    a body having a longitudinal axis, a locking member movable at an angle with respect to said longitudinal axis, an end connected to said pierceable access port, and a needle-less access septum at an opposing end of said body, said locking member disposed between said ends and being movable from an unlocked position on said body to a locked position for preventing movement of said body relative to said pierceable access port;
    an access member carried by said body for piercing said pierceable access port, said body enclosing said access member sufficiently to prevent inadvertent user contact therewith; and
    an administration set having a first end for receiving the fluid source and a second end connected to said body.

18. The connector of claim 17 wherein said needle-less access septum allows fluid flow between the body and the administration set upon insertion of a blunt cannula into the needle-less access septum and prevents fluid flow between the body and the administration set when the blunt cannula is removed from the needle-less access septum.

19. A method of facilitating fluid communication between a sealed container or other medical fluid flow device having a pierceable access port and at least one fluid passageway, comprising:
    providing a connector with an elongated body and a locking member disposed between a first end and a second end of said elongated body, said connector further including a piercing member for piercing the pierceable access port, said body enclosing said piercing member sufficiently to prevent inadvertent user contact therewith;
    attaching said elongated body to the pierceable access port; and
    attaching a needle-less end of an administration set to said elongated body having a locking member associated with said elongated body and movable at an angle with respect to said elongated body between an unlocked position on the elongated body and a locked position for preventing movement of said elongated body relative to the pierceable access port.

20. A connector for transferring a fluid between a fluid injecting device and a pierceable access port of a container or other fluid flow device comprising:
    an elongated body having a first end with a needle-less access septum configured for receiving a needle-free fluid injecting device that injects fluid into said elongated body and a second end for receiving the pierceable access port of the container; means for transferring the fluid injected into said elongated body to the pierceable access port, wherein said transferring means is in fluid communication with the needle-less access septum and a portion of the body at least partially encloses said transferring means to prevent inadvertent user contact therewith; and
    means for preventing movement of said elongated body relative to the pierceable access port to facilitate transfer of the fluid to the pierceable access port, wherein the means for preventing movement of said elongated body comprises a locking member disposed between said first and second ends and movable at an angle with respect to the elongated body between a first or unlocked position contacting the elongated body and a second or locked position, and wherein said means for transferring the fluid comprises a needle connected to an inner surface of said elongated body that defines an inner chamber for receiving the fluid from the fluid injecting device and allows transfer of the fluid from the container to an end source, and wherein said needle has a pointed end enclosed by said elongated body.

* * * * *